(12) United States Patent
Kume et al.

(10) Patent No.: US 9,506,899 B2
(45) Date of Patent: Nov. 29, 2016

(54) GAS SENSOR

(71) Applicant: NGK SPARK PLUG CO., LTD., Nagoya-shi, Aichi (JP)

(72) Inventors: Makoto Kume, Inuyama (JP); Shingo Ito, Ichinomiya (JP); Daisuke Tahira, Komaki (JP); Takehiro Oba, Konan (JP); Yuichi Yamada, Komaki (JP)

(73) Assignee: NGK SPARK PLUG CO., LTD., Aichi (JP)

(*) Notice: Subject to any disclaimer, the term of this patent is extended or adjusted under 35 U.S.C. 154(b) by 330 days.

(21) Appl. No.: 14/252,073

(22) Filed: Apr. 14, 2014

(65) Prior Publication Data

US 2014/0305188 A1  Oct. 16, 2014

(30) Foreign Application Priority Data

Apr. 15, 2013  (JP) ................ 2013-084699

(51) Int. Cl.
*G01N 33/00* (2006.01)
*G01N 27/407* (2006.01)

(52) U.S. Cl.
CPC ...... *G01N 33/0009* (2013.01); *G01N 27/4077* (2013.01)

(58) Field of Classification Search
CPC .................................................. G01N 33/009
USPC ............ 73/23.2, 23.31, 23.33, 31.01, 31.03, 73/31.05
See application file for complete search history.

(56) References Cited

U.S. PATENT DOCUMENTS

| 5,880,353 | A | 3/1999 | Graser et al. |
| 7,013,701 | B2 | 3/2006 | Kawashima |
| 7,407,567 | B2 | 8/2008 | Furuta et al. |
| 7,943,025 | B2 | 5/2011 | Ohly et al. |
| 8,623,187 | B2 | 1/2014 | Horisaka et al. |
| 2004/0123642 | A1 | 7/2004 | Kawashima |
| 2007/0017806 | A1 | 1/2007 | Furuta et al. |

(Continued)

FOREIGN PATENT DOCUMENTS

| DE | 10 2008 041 038 A1 | 2/2010 | |
| DE | 102008041038 | * 2/2010 | ........... G01N 27/403 |
| JP | 61-159150 A | 7/1986 | |
| JP | 11-505029 A | 5/1999 | |
| JP | 2000-171430 A | 6/2000 | |

(Continued)

OTHER PUBLICATIONS

Communication dated Feb. 23, 2016 from the Japanese Patent Office issued in corresponding Japanese Application No. 2013-084699.

*Primary Examiner* — Hezron E Williams
*Assistant Examiner* — Hoang Nguyen
(74) *Attorney, Agent, or Firm* — Sughrue Mion, PLLC

(57) ABSTRACT

A protector (160) is inserted into a metallic shell (110) such that at least a portion of each gas introduction hole (167) is located on the base end side with respect to the forward end (110b) of the metallic shell. The metallic shell has a gas introduction space S2 defined by a forward-end-side inner surface (113b) of the metallic shell and an outer surface (160d) of the protector and which guides a gas-to-be-detected (exhaust gas G) from a region on the forward end side of the metallic shell into the gas introduction holes of the protector. The base end of the forward end portion (121) of the detection element (120) is located on the base end side with respect to the forward end (167b) of each gas introduction hole, and the forward end of the forward end portion is located on the forward end side with respect to the base end (167c) of each gas introduction hole.

6 Claims, 9 Drawing Sheets

(56) References Cited

U.S. PATENT DOCUMENTS

| | | |
|---|---|---|
| 2008/0296156 A1 | 12/2008 | Ohly et al. |
| 2009/0100907 A1* | 4/2009 | Mizutani ............ G01N 27/4077 73/31.05 |
| 2011/0233060 A1 | 9/2011 | Horisaka et al. |
| 2012/0145543 A1* | 6/2012 | Sugaya .............. G01N 27/4074 204/424 |
| 2015/0101394 A1* | 4/2015 | Fujita ................ G01N 27/4077 73/23.31 |

FOREIGN PATENT DOCUMENTS

| | | |
|---|---|---|
| JP | 2002-5877 A | 1/2002 |
| JP | 2004-191328 A | 7/2004 |
| JP | 2004-257890 A | 9/2004 |
| JP | 2007-33114 A | 2/2007 |
| JP | 2008-298781 A | 12/2008 |
| JP | 2009-97868 A | 5/2009 |
| JP | 2011-227061 A | 11/2011 |
| JP | 2012-242284 A | 12/2012 |

* cited by examiner

GAS SENSOR

BACKGROUND OF THE INVENTION

1. Field of the Invention

The present invention relates to a gas sensor including a detection element which is exposed to a gas-to-be-detected in order to detect a particular gas component contained in the gas-to-be-detected.

2. Description of the Related Art

A gas sensor has conventionally been known which is attached to an exhaust pipe of an automobile or the like. The gas sensor includes a detection element which generates an electromotive force whose magnitude changes in accordance with the concentration of a particular gas, such as NOx (nitrogen oxides) or oxygen, contained in a gas-to-be-detected (exhaust gas), or which changes as the resistance of the detection element changes in accordance with the concentration of the particular gas. Patent Documents 1 and 2 disclose such a gas sensor which includes a detection element extending from a base end side toward a forward end side in an axial direction thereof; a tubular metallic shell which surrounds the circumference of the detection element; and a tubular protector (inner protector) provided on the forward end side of the metallic shell and surrounding the circumference of a forward end portion of the detection element.

The forward end portion of the detection element has a detection section which has a gas passage portion which allows the gas-to-be-detected to pass therethrough. The above-described gas sensor detects a particular gas component contained in the gas-to-be-detected which is introduced into the interior of the detection element through the gas passage portion of the detection section. The protector (the inner protector) has gas introduction holes which are located on the base end side with respect to the forward end of the detection element and which introduces the gas-to-be-detected from the outside of the protector into the interior of the protector, and a gas discharge hole which is located on the forward end side with respect to the forward end of the detection element and which discharges the gas-to-be-detected from the interior of the protector to the outside of the protector. Notably, the forward end portion of the detection element projects forward from the metallic shell such that the entire gas passage portion is located on the forward end side with respect to the forward end of the metallic shell.

[Patent Document 1] Japanese Patent Application Laid-Open (kokai) No. 2009-97868

[Patent Document 2] DE 10 2008 041 038 A1

3. Problems to be Solved by the Invention

In recent years, there has been demand to decrease the length of the detection element so as to reduce cost. This is because the amount of platinum used to form electrodes, lead portions, etc., on the detection element can be reduced by decreasing the length of the detection element. In the case where the length of the detection element is decreased in the gas sensor disclosed in Patent Document 1, a forward end portion (a portion where a gas passage portion is provided) of the detection element is preferably located closer to the base end side (the side toward the metallic shell), while a rear end portion (a portion where connection pads are provided) of the detection element is arranged as far as possible from the forward end of the metallic shell. This is because, if connection terminals connected to the connection pads provided on the base end portion of the detection element are too close to the forward end of the gas sensor, the connection terminals deteriorate due to the influence of heat from the exhaust pipe, and the reliability of electrical continuity between the connection pads and the connection terminals is more likely to decrease.

In order to overcome such a drawback, in the gas sensor disclosed in Patent Document 1, a portion of the detection element located on the forward end side thereof is shortened such that at least a portion of the detection section (the gas passage portion) of the detection element is disposed on the base end side with respect to the forward end of the metallic shell. In this case, the detection section (the gas passage portion) of the detection element is disposed on the base end side with respect to the gas introduction holes of the inner protector. Incidentally, the gas-to-be-detected having been introduced into the interior of the inner protector through the gas introduction holes of the inner protector flows toward the forward end side, and is discharged to the outside through the gas discharge hole provided on the forward end side of the inner protector. Therefore, if the gas sensor of Patent Document 1 is configured such that at least a portion of the detection section (the gas passage portion) of the detection element is located on the base end side with respect to the forward end of the metallic shell, it is difficult for the gas-to-be-detected to flow along the detection section (the gas passage portion), and, as a result, the responsiveness of the gas sensor may deteriorate.

Meanwhile, in the gas sensor disclosed in Patent Document 2, a gas introduction space is formed on the forward end side of the interior of the metallic shell. The gas introduction space is concave toward the base end side. By virtue of this configuration, in the gas sensor disclosed in Patent Document 2, the gas-to-be-detected is introduced into the gas introduction space inside the metallic shell through the gas introduction holes of the inner protector, and then flows toward the forward end side. Therefore, in the gas sensor disclosed in Patent Document 2, even when at least a portion of the detection section (the gas passage portion) of the detection element is disposed on the base end side with respect to the forward end of the metallic shell, after being introduced into the gas introduction space inside the metallic shell through the gas introduction holes of the inner protector, the gas-to-be-detected can flow along the detection section (the gas passage portion) of the detection element.

However, in the gas sensor disclosed in Patent Document 2, since the gas-to-be-detected is introduced into the gas introduction space inside the metallic shell after passing through the gas introduction holes of the inner protector, conceivably, the gas-to-be-detected flows turbulently in the gas introduction space. Therefore, the gas-to-be-detected flows turbulently around the forward end portion of the detection element as well, and the gas-to-be-detected may fail to smoothly flow along the detection section (the gas passage portion). Therefore, the responsiveness of the gas sensor disclosed in Patent Document 2 is also susceptible to deterioration.

SUMMARY OF THE INVENTION

The present invention was made to solve the above problems, and an object thereof is to provide a gas sensor which has excellent responsiveness in spite of at least a portion of a detection section of a detection element being located on the base end side with respect to the forward end of a metallic shell.

The above object of the invention has been achieved by providing (1) a gas sensor comprising a detection element which extends from a base end side to a forward end side in an axial direction, which detects a particular gas component contained in a gas-to-be-detected, and which has a detection section on the forward end side; a tubular metallic shell which surrounds a circumference of the detection element; and a tubular protector which surrounds a circumference of a forward end portion of the detection element. The protector has a gas introduction hole located on the base end side with respect to a forward end of the detection element and which introduces the gas-to-be-detected from outside of the protector into the interior thereof, and a gas discharge hole located on the forward end side with respect to the forward end of the detection element and which discharges the gas-to-be-detected from the interior of the protector to the outside thereof. In the gas sensor, at least a portion of the detection section of the detection element is located on the base end side with respect to a forward end of the metallic shell; the protector is inserted into the interior of the metallic shell in a state in which at least a portion of the gas introduction hole is located on the base end side with respect to the forward end of the metallic shell; a forward-end-side inner surface of the metallic shell and an outer surface of the protector form therebetween a gas introduction space for guiding the gas-to-be-detected from a region on the forward end side with respect to the metallic shell to the gas introduction hole of the protector; and a base end of the detection section of the detection element is located on the base end side with respect to a forward end of the gas introduction hole, and a forward end of the detection section is located on the forward end side with respect to a base end of the gas introduction hole.

In the above-described gas sensor, at least a portion of the detection section of the detection element is located on the base end side with respect to the forward end of the metallic shell. In other words, the base end of the detection section is located on the base end side with respect to the forward end of the metallic shell. In such a case, as described above with respect to the gas sensor of Patent Document 1, it may be difficult for the gas-to-be-detected to flow along the detection section such that the responsiveness of the gas sensor deteriorates.

In contrast, in the above-described gas sensor, a base end portion of the protector is inserted into the metallic shell. This configuration enables at least a portion of the gas introduction hole of the protector to be disposed on the base end side with respect to the forward end of the metallic shell (namely, in the interior of the metallic shell).

In addition, in the above-described gas sensor, the forward-end-side inner surface of the metallic shell and the outer surface of the protector form a gas introduction space (between the forward-end-side inner surface and the outer surface). This gas introduction space is a space for introducing the gas-to-be-detected from a region on the forward end side of the metallic shell into the gas introduction hole of the protector.

Namely, at least a portion of the gas introduction hole of the protector is exposed to the gas introduction space. In other words, the base end of the gas introduction hole of the protector is located on the base end side with respect to the forward end of the metallic shell, and at least a portion of the gas introduction hole is exposed to the gas introduction space.

By virtue of such a structure, in the above-described gas sensor, the gas-to-be-detected (at least a portion thereof) can be introduced into the gas introduction space of the metallic shell, and then introduced into the interior of the protector through the gas introduction hole of the protector.

As a result, in the above-described gas sensor, the gas-to-be-detected introduced from outside into the gas introduction space is introduced into the interior of the protector through the gas introduction hole of the protector, flows along the forward end portion (a portion including the detection section) of the detection element, and is then discharged to the outside of the protector through the gas discharge hole located on the forward end side with respect to the forward end of the detection element. In addition, as viewed in the axial direction of the detection element, the base end of the detection section of the detection element is located on the base end side with respect to the forward end of the gas introduction hole of the protector, and the forward end of the detection section is located on the forward end side with respect to the base end of the gas introduction hole of the protector. By virtue of this positional relation, a portion of the gas-to-be-detected introduced into the interior of the protector through the gas introduction hole can properly flow along the detection section.

In addition, since the gas-to-be-detected passes through the gas introduction hole of the protector after having been introduced into the gas introduction space, the flow of the gas-to-be-detected assumes a straightened flow (laminar flow). Thus, in the above-described gas sensor, the flow of the gas-to-be-detected assumes a straightened flow (laminar flow) around the detection section of the detection element. This is because, unlike the above-described gas sensor of Patent Document 2, after passing through the gas introduction hole of the protector, the gas-to-be-detected flows toward the detection element (the detection section) without passing through the gas introduction space of the metallic shell. As a result, the gas-to-be-detected can smoothly flow along the detection section. Accordingly, the above-described gas sensor can have excellent responsiveness.

Notably, the "detection element" of the invention may be a plate-shaped detection element which extends from the base end side to the forward end side in the axial direction or a tubular detection element which extends from the base end side to the forward end side in the axial direction and which has a reference space therein.

In a preferred embodiment (2), the gas sensor (1) above is configured such that the detection section has a gas passage portion which allows passage of the gas-to-be-detected therethrough; at least a portion of the gas passage portion is located on the base end side with respect to the forward end of the metallic shell; and a base end of the gas passage portion is located on the base end side with respect to the forward end of the gas introduction hole, and a forward end of the gas passage portion is located on the forward end side with respect to the base end of the gas introduction hole.

The above-described gas sensor provides the following advantageous effects. Even in the case where a detection element having a gas passage portion at the detection section thereof is used, by virtue of the above-described positional relation, a portion of the gas-to-be-detected introduced into the interior of the protector through the gas introduction hole can properly flow along the gas passage portion. In addition, since the flow of the gas-to-be-detected assumes a straightened flow (laminar flow) as a result of passing through the gas introduction hole of the protector after having been introduced into the gas introduction space, in the above-described gas sensor, the flow of the gas-to-be-detected assumes a straightened flow (laminar flow) around the gas passage portion of the detection element. As a result, the gas-to-be-detected can smoothly flow along the gas passage portion. Accordingly, the above-described gas sensor can have excellent responsiveness.

Notably, the "gas passage portion" of the invention may be a passage which connects together a measurement chamber provided in the detection element and the outside of the detection element, or a porous portion provided in the passage. Alternatively, the gas passage portion may be a porous portion that is exposed on the surface of the detection element and which intervenes between an electrode provided inside the detection element and the outside of the detection element.

In another preferred embodiment (3), the gas sensor (1) or (2) above is configured such that the forward-end-side inner surface of the metallic shell which forms the gas introduction space has a taper surface whose diameter decreases from the forward end side toward the base end side.

The above-described gas sensor provides the following advantageous effect. Since the gas-to-be-detected introduced into the gas introduction space is more likely to flow radially inward along the taper surface, the gas-to-be-detected is more likely to be introduced into the interior of the protector through the gas introduction hole of the protector, which is located on the radially inner side of the taper surface. As a result, the responsiveness of the gas sensor is enhanced.

In yet another preferred embodiment (4), the gas sensor of any of (1) to (3) above is configured such that the base end of the gas introduction hole of the protector is located at a position which is the same as, or is shifted toward the base end side from, the position of a base end of the gas introduction space in the axial direction.

In the case where a portion of the gas introduction space is present on the base end side with respect to the gas introduction hole of the protector; namely, in the case where the base end of the gas introduction hole of the protector is located on the forward end side with respect to the base end of the gas introduction space, the gas-to-be-detected may stagnate in a portion of the gas introduction space which is located on the base end side with respect to the gas introduction hole of the protector, and the gas-to-be-detected may not be smoothly introduced into the interior of the protect through the gas introduction hole of the protector.

In contrast, in the above-described gas sensor, as viewed in the axial direction, the base end of the gas introduction hole of the protector is located at a position which is the same as the position of the base end of the gas introduction space (corresponding to the base end of the forward-end-side inner surface of the metallic shell which forms the gas introduction space) or which is shifted toward the base end side from the base end of the gas introduction space. Therefore, in the above-described gas sensor, the gas-to-be-detected introduced into the gas introduction space is more likely to be smoothly introduced into the interior of the protector through the gas introduction hole of the protector. As a result, the responsiveness of the gas sensor is enhanced.

In yet another preferred embodiment (5), the gas sensor of any one of (1) to (4) above further comprises an outer protector which covers a circumference of the protector and which is welded to the metallic shell, wherein the protector is fixedly press-fitted into the outer protector.

The circumference of the protector is covered with the outer protector to protect the detection element from being directly exposed to the gas-to-be-detected. Therefore, it is possible to prevent the detection element from cracking, which would otherwise occur if water contained in the gas-to-be-detected were to be adhered to the detection element.

In addition, the protector and the outer protector are fixed together through press-fitting, and the outer protector is welded to the metallic shell to fix the same. Therefore, the circumference of the protector can be readily covered with the outer protector.

In yet another preferred embodiment (6), the gas sensor of any of (1) to (5) above is configured such that, as viewed in the axial direction, the forward end of the detection element is disposed on the base end side of a position spaced 5 mm forward from the forward end of the metallic shell.

In the above-described gas sensor, the projection length by which the forward end of the detection element projects from the forward end of the metallic shell is set to be 5 mm or less. This gas sensor also has excellent responsiveness similar to the above-described gas sensor (1) above.

DESCRIPTION OF REFERENCE NUMERALS

Figure 1:
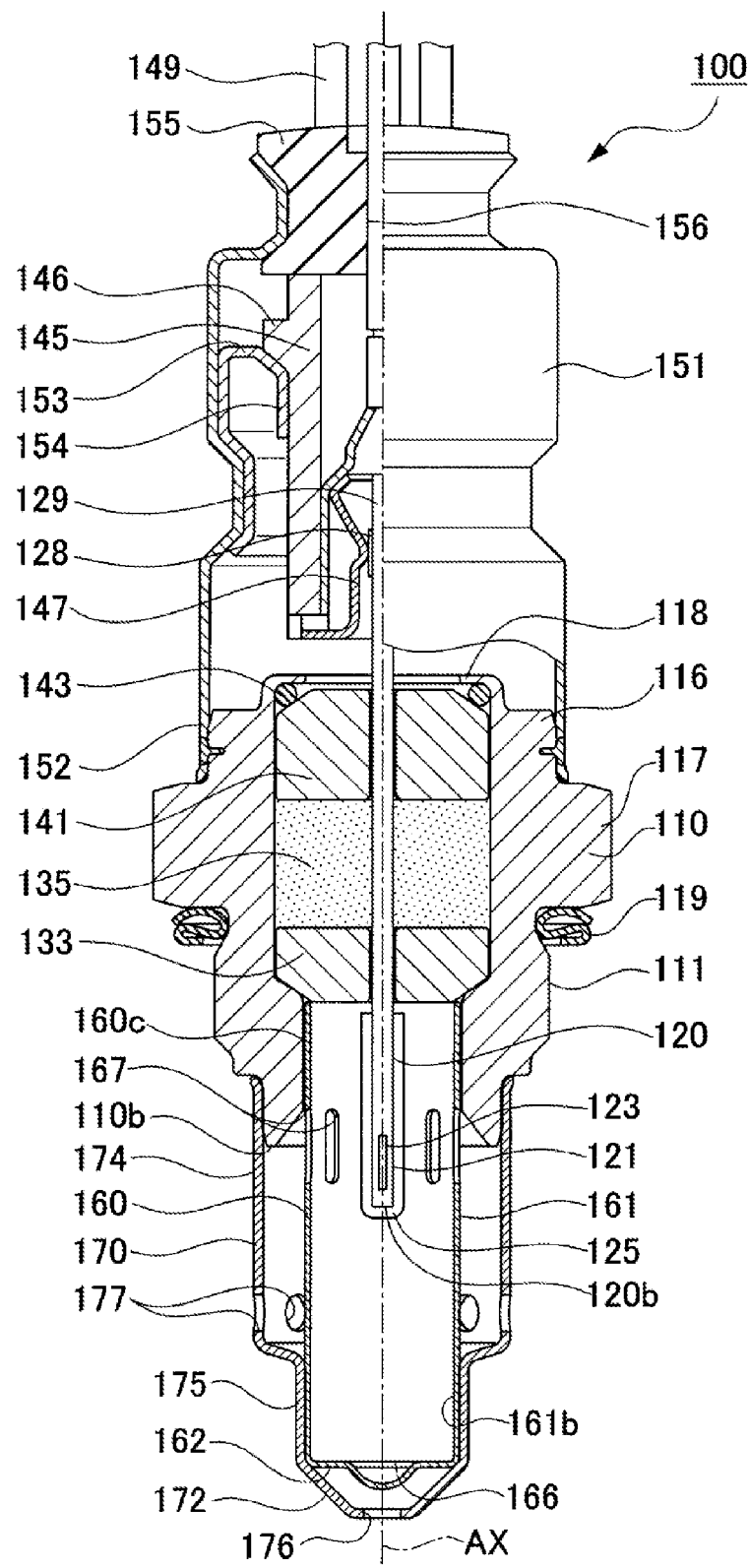
FIG. 1 is a partial sectional view of a gas sensor according to an embodiment of the invention.

Reference numerals used to identify various features in the drawings include the following.

100, 200, 300: gas sensor
110, 310: metallic shell
110$b$, 310$b$: forward end of the metallic shell
113, 313: forward end portion of the metallic shell
113$b$: forward-end-side inner surface (taper surface) of the metallic shell
120: detection element
121: forward end portion of the detection element
123: gas passage portion
160, 260: inner protector (protector)
160$c$, 260$c$: base end portion of the inner protector
166, 266: gas discharge hole of the inner protector
167, 267: gas introduction hole of the inner protector
170: outer protector
176: gas discharge hole of the outer protector
177: gas introduction hole of the outer protector
313$b$: forward-end-side inner surface of the metallic shell
313$c$: taper surface of the metallic shell
360: protector
360$c$: base end portion of the protector
366: gas discharge hole of the protector
367: gas introduction hole of the protector
AX: axis
G: exhaust gas (gas-to-be-detected)
S2: gas introduction space

DETAILED DESCRIPTION OF THE PREFERRED EMBODIMENTS

An embodiment of the present invention will next be described with reference to the drawings. However, the present invention should not be construed as being limited thereto.

Figure 2:
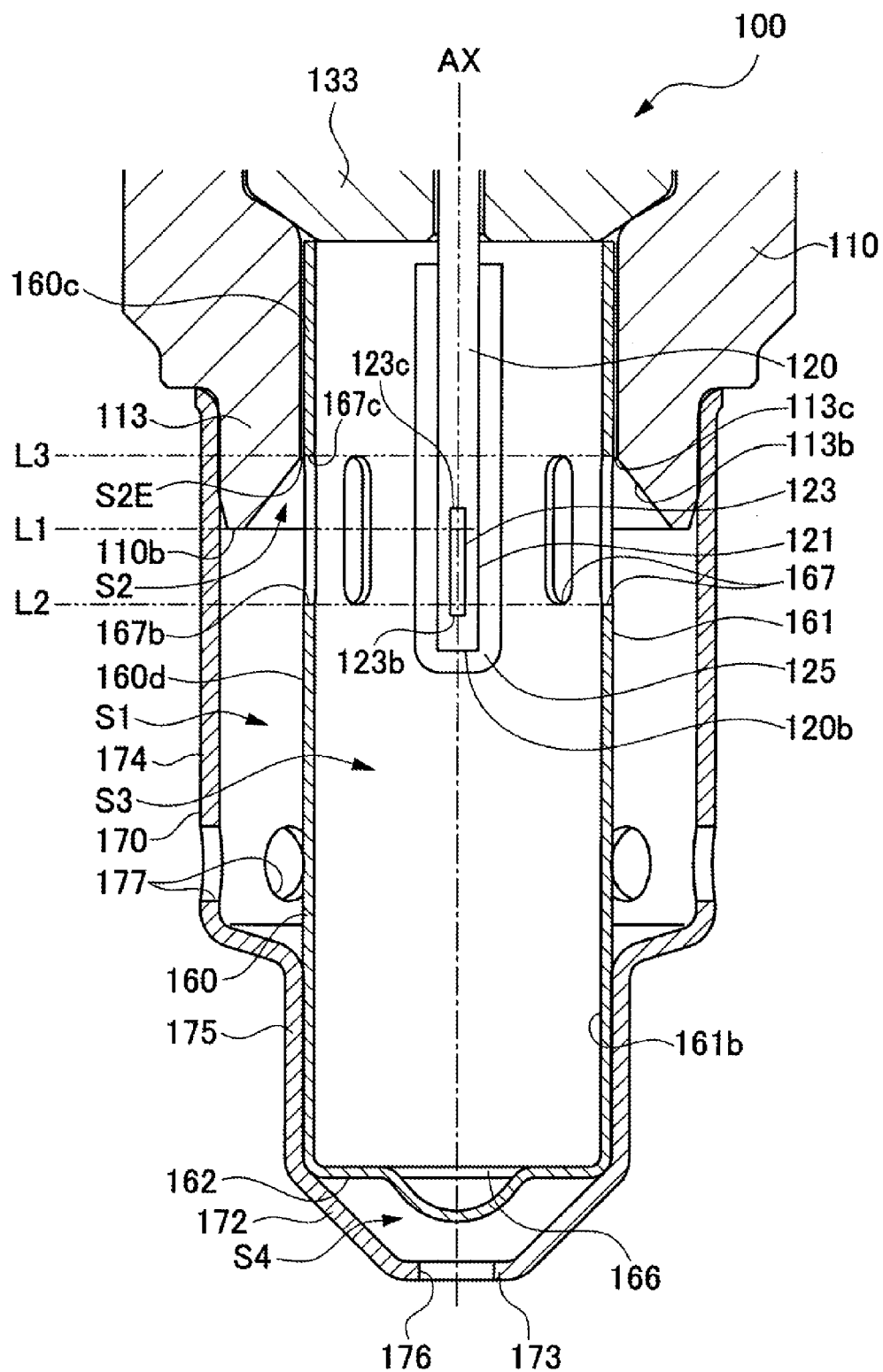
FIG. 2 is an enlarged sectional view of a forward end portion of the gas sensor of the embodiment.
Figure 3:
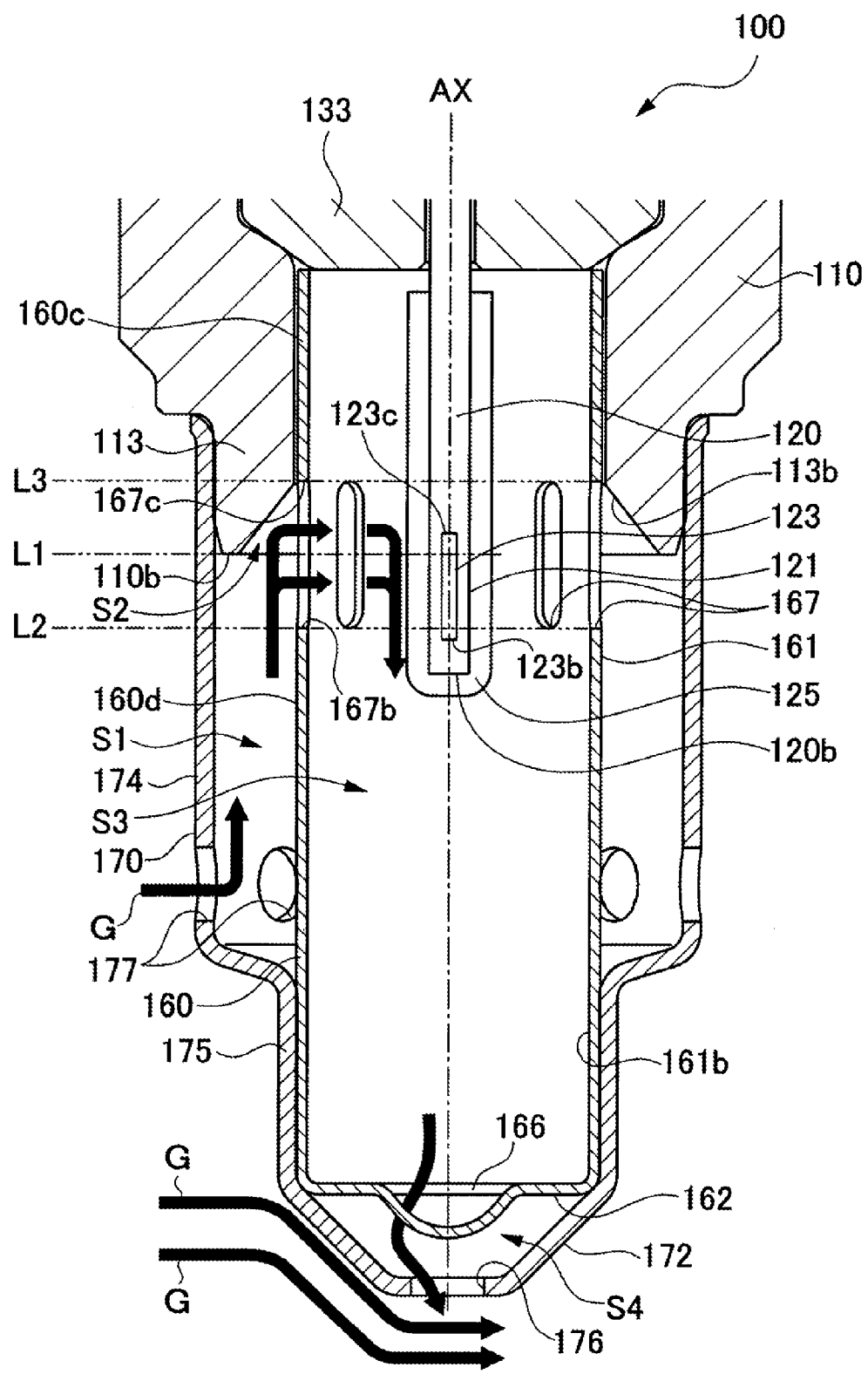
FIG. 3 is a view describing a flow of a gas-to-be-detected within the gas sensor of the embodiment.

FIG. 1 is a partial sectional view of a gas sensor 100 of the present embodiment. FIG. 2 is an enlarged sectional view of a forward end portion of the gas sensor 100. FIG. 3 is a sectional view showing, on an enlarged scale, a forward end portion of the gas sensor 100 attached to an exhaust pipe of an unillustrated automobile such that the forward end portion of the gas sensor 100 is located within the exhaust pipe. FIG. 3 is a view describing the flow of exhaust gas (gas-to-be-detected) G.

Notably, in FIGS. 1 to 3, the lower side is an axially forward end side (hereinafter also referred to as the forward end side), and the upper side is an axially base end side (hereinafter also referred to as the base end side). Also, in FIG. 3, the left side is the upstream side (engine side) of the exhaust pipe through which exhaust gas G flows, and the right side is the downstream side of the exhaust pipe.

The gas sensor 100 is a so-called full range air/fuel ratio sensor which is attached to the exhaust pipe of an unillustrated automobile and which holds therein a detection element 120. A forward end portion 121 of the detection element 120 is exposed to the exhaust gas (gas-to-be-detected) which flows through the exhaust pipe so as to detect the air/fuel ratio of the exhaust gas from the concentration of oxygen (particular gas component) contained in the exhaust gas.

Notably, in the present embodiment, the forward end portion 121 corresponds to the "detection section" of the invention.

As shown in FIG. 1, this gas sensor 100 is mainly composed of a tubular metallic shell 110 extending in an axial direction (the direction along an axis AX, the vertical direction in FIG. 1); the plate-shaped detection element 120 held inside the metallic shell 110; an outer tube 151 fixedly provided on the base end side of the metallic shell 110; and an inner protector 160 and an outer protector 170 which are fixedly provided on the forward end side of the metallic shell 110; etc.

The detection element 120 has a plate-like shape (strip-like shape) extending in the axial direction, and detects the oxygen gas component contained in the exhaust gas G (see FIG. 1). This detection element 120 has a known structure and is formed by bonding together for unification a plate-shaped gas detecting body for detecting oxygen concentration and a plate-shaped heater body for heating the gas detecting body for quick activation thereof. The gas detecting body is composed of a solid electrolyte body which predominantly contains zirconia, and a pair of electrodes (detection and reference electrodes) which predominantly contain platinum. The pair of electrodes are disposed on the forward end portion 121 of the detection element 120.

At least one gas passage portion 123 is provided at the forward end portion 121 of the detection element 120 so as to introduce the exhaust gas G from outside of the detection element 120 into an interior (gas measurement chamber) thereof, to thereby allow detection of the oxygen component contained in the exhaust gas G. The gas passage portion 123 is formed of a porous material and has a rectangular shape in plan view. In the present embodiment, two gas passage portions 123 having the same dimensions are provided at the same position in the axial direction (the gas passage portion 123 shown in FIG. 1 and another gas passage portion located on the back side thereof are provided). At least a portion of each gas passage portion 123 is located on the base end side (on the upper side in FIGS. 1 and 2) in relation to the forward end 110b of the metallic shell 110. Notably, in FIG. 2, the position of the forward end 110b of the metallic shell 110 in the axial direction is indicated by a straight line L1. FIG. 2 clearly shows that a portion of the gas passage portion 123 is located on the base end side with respect to the straight line L1.

Five electrode pads 128 (one of which is shown in FIG. 1) for allowing external connection with the electrodes of the gas detecting body and the heater body are formed on a base end portion 129 of the detection element 120.

In order to protect the detection electrode from poisoning by the exhaust gas, a protection layer 125 is provided on the forward end portion 121 of the detection element 120 such that the protection layer 125 covers the outer surface of the forward end portion 121 (see FIG. 1).

In the gas sensor 100, a ceramic ring 133 made of alumina, a talc ring 135 formed by compacting a talc powder, and a tubular sleeve 141 are accommodated inside the metallic shell 110 in such a manner that the detection element 120 is inserted through the ceramic ring 133, the talc ring 135 and the sleeve 141. The talc ring 135 is compacted within the metallic shell 110 so as to tightly fill an associated space. As a result, the detection element 120 is positioned and held in the tubular metallic shell 110 which surrounds the circumference of the detection element 120. Notably, in the present embodiment, as viewed in the axial direction, the forward end 120b of the detection element 120 is disposed on the base end side of a position spaced 5 mm forward from the forward end 110b of the metallic shell 100. More specifically, the projection length by which the detection element 120 projects from the forward end 110b of the metallic shell 100 is set to be 5 mm or less.

The metallic shell 110 is adapted to fixedly attach the gas sensor 100 to the exhaust pipe of the automobile. An external thread portion 111 for attachment to the exhaust pipe is formed on the forward end side of the outer circumference of the metallic shell 110. The inner protector 160 and the outer protector 170, described below, are provided on the forward end side of the metallic shell 110.

The metallic shell 110 also has a tool engagement portion 117 which is formed at the center of the outer circumference of the metallic shell 110 and with which a mounting tool is engaged. In order to prevent leakage of gas when the gas sensor 100 is attached to the exhaust pipe, a gasket 119 is fitted to a portion of the metallic shell 110 between the tool engagement portion 117 and the external thread portion 111. The metallic shell 110 further has a base end fixing portion 116 which is formed on the base end side of the tool engagement portion 117 and to which the outer tube 151 to be described below is fixed. The metallic shell 110 further has a crimp portion 118 which is formed on the base end side of the base end fixing portion 116 and which is adapted to crimp-hold the detection element 120 in the metallic shell 110. An annular crimp packing 143 is disposed between the crimp portion 118 and the sleeve 141.

A base end portion 129 of the detection element 120 projects toward the base end side beyond the crimp portion 118, which is the base end portion of the metallic shell 110. The base end portion 129 is covered with a tubular separator 145 formed from an electrically insulative ceramic. The separator 145 internally holds five connection terminals 147 (one of which is shown in FIG. 1) electrically connected to the five electrode pads 128 formed on the base end portion 129 of the detection element 120. Also, the separator 145 accommodates connection portions between the connection terminals 147 and corresponding five lead wires 149 (three of which are shown in FIG. 1), which extend to the exterior of the gas sensor 100, while insulating the terminals and corresponding lead wires from one another.

The tubular outer tube 151 is disposed so as to surround the circumference of the separator 145. The outer tube 151 is made of stainless steel (SUS304 in the present embodiment). A forward end opening portion 152 of the outer tube 151 is disposed on the radially outer side of the base end fixing portion 116 of the metallic shell 110. The forward end opening portion 152 is joined to the base end fixing portion 116 by laser welding.

A tubular metal holder 153 is disposed in the gap between the outer tube 151 and the separator 145. The metal holder 153 has a support portion 154, which is formed by inwardly bending a base end of the metal holder 153. The separator 145 is inserted through the metal holder 153 such that a flange portion 146 formed on the outer circumference of a base end portion of the separator 145 is engaged with the support portion 154, whereby the separator 145 is supported by the support portion 154. In this condition, a portion of the outer tube 151 where the metal holder 153 is disposed is crimped radially inward, whereby the metal holder 153 which supports the separator 145 is fixed to the outer tube 151.

A grommet 155 made of a fluorine-containing rubber is fitted into a base end opening of the outer tube 151. The grommet 155 has five insertion holes 156 (one of which is shown in FIG. 1). The five lead wires 149 extending outwardly from the separator 145 are airtightly inserted through the respective insertion holes 156. In this condition, while the grommet 155 presses the separator 145 toward the forward end side, a portion of the outer tube 151 which corresponds to the grommet 155 is crimped radially inward, whereby the grommet 155 is fixed to the outer tube 151.

The tubular inner and outer protectors 160 and 170, which surround the circumference of the forward end portion 121 of the detection element 120, are provided on the forward end side of the metallic shell 110. The inner and outer protectors 160 and 170 protect the forward end portion 121 of the detection element 120 from contamination caused by deposits (poisoning adhesive substances such as fuel ash and oil component) contained in exhaust gas and from breakage caused by water adhering thereto.

Notably, in the present embodiment, the inner protector 160 corresponds to the "protector" of the invention.

The inner protector 160 has a cylindrical tubular side wall portion 161 which extends in the axial direction (the direction along the axis AX), and a disk-shaped bottom portion 162 which closes the forward end side of the side wall portion 161. Gas introduction holes 167 for introducing the gas-to-be-detected from the outside of the inner protector 160 into the interior thereof are formed in the side wall portion 161 at positions on the base end side (on the upper side in FIGS. 1 and 2) in relation to the forward end 120b of the detection element 120. Notably, in the present embodiment, eight gas introduction holes 167 having the same dimension are formed at equal intervals in the circumferential direction of the side wall portion 161 at the same position in the axial direction. At least a portion of each of these gas introduction holes 167 is located on the base end side with respect to the forward end 110b of the metallic shell 110.

Further, the inner protector 160 has a gas discharge hole 166 for discharging the gas-to-be-detected from the interior of the inner protector 160 to the outside thereof. The gas discharge hole 166 is located on the forward end side (on the lower side in FIGS. 1 and 2) with respect to the forward end 120b of the detection element 120. More specifically, the gas discharge hole 166 is provided in the bottom portion 162 of the inner protector 160.

The outer protector 170 is fixed to the metallic shell 110 in a state in which the inner protector 160 is fixed to the inner side of the outer protector 170. Specifically, the outer protector 170 is joined to the metallic shell 110 by laser welding. The outer protector 170 has a first side wall portion 174; a second side wall portion 175 located on the axially forward end side of the first side wall portion 174, a taper wall 172 located on the axially forward end side of the second side wall portion 175, and a bottom portion 173 located on the forward end side of the taper wall 172 (see FIGS. 1 and 2).

The first side wall portion 174 has a cylindrical tubular shape, and surrounds the circumference of the side wall portion 161 of the inner protector 160 while forming a space S1 between the first side wall portion 174 and the side wall portion 161. The first wall portion 174 has gas introduction holes 177 which penetrate the first wall portion 174 and are located on the axially forward end side with respect to the gas introduction holes 167 of the inner protector 160 (see FIGS. 1 and 2). Notably, in the present embodiment, eight gas introduction holes 177 are formed at equal intervals in the circumferential direction. All the eight gas introduction holes 177 are located on the axially forward end side with respect to the gas introduction holes 167 of the inner protector 160.

The second wall portion 175 has a cylindrical tubular shape, and has an inner diameter smaller than the inner diameter of the first wall portion 174 and larger than the outer diameter of the side wall portion 161 of the inner protector 160. A forward end portion 161b of the side wall portion 161 of the inner protector 160 is press-fitted into the second side wall portion 175. As a result, the inner protector 160 is fixed to the inner side of the outer protector 170, and the second side wall portion 175 of the outer protector 170 and the forward end portion 161b of the side wall portion 161 of the inner protector 160 are gastightly connected (fitted) together over the entire circumference around the axis AX.

The taper wall 172 has the shape of a tapered tube (truncated conical tube) whose diameter decreases toward the axially forward end side. The bottom portion 173 has a gas discharge hole 176, which is a forward end opening of the outer protector 170. The taper wall 172 and the bottom portion 173 form a space S4 in cooperation with the bottom portion 162 of the inner protector 160 (see FIG. 2).

Incidentally, in the gas sensor 100 of the present embodiment, at least a portion of the forward end portion 121 (the gas passage portions 123) of the detection element 120 is located on the base end side (on the upper side in FIG. 2) in relation to the forward end 110b of the metallic shell 110. In other words, the base end of the forward end portion 121 (for example, the base end 123c of each gas passage portion 123) is located on the base end side with respect to the forward end 110b of the metallic shell 110. In this case, as described above, in the case of the gas sensor of Patent Document 1, it is difficult for the gas-to-be-detected to flow along the detection section (pass through the gas passage portion) and reach a gas measurement chamber within the detection element. Therefore, the responsiveness of the gas sensor may deteriorate.

In contrast, in the case of the gas sensor 100 of the present embodiment, the base end portion 160c of the inner protector 160 is disposed in (inserted into) the space inside the metallic shell 110 as shown in FIG. 2. This configuration enables at least a portion of each gas introduction hole 167 of the inner protector 160 to be disposed on the base end side with respect to the forward end 110b of the metallic shell 110 (namely, in the interior of the metallic shell 110).

In addition, a forward-end-side inner surface 113b of a forward end portion 113 of the metallic shell 110 is concaved radially outward, and forms a gas introduction space S2 in cooperation with the outer surface 160d of the inner protector 160 (between the forward-end-side inner surface 113b and the outer surface 160d). This gas introduction space S2 is a space for introducing the exhaust gas G (the gas-to-be-detected) from a region on the forward end side of the metallic shell 110 into the gas introduction holes 167 of the inner protector 160.

Namely, at least a portion of each gas introduction hole 167 of the inner protector 160 is exposed to the gas introduction space S2. In other words, the base end 167c of each gas introduction hole 167 is located on the base end side with respect to the forward end 110b of the metallic shell 110, and at least a portion of the gas introduction hole 167 is exposed to the gas introduction space S2.

By virtue of such a structure, in the gas sensor 100 of the present embodiment, as indicated by arrows in FIG. 3, the exhaust gas G (at least a portion thereof) can be introduced into the gas introduction space S2 of the metallic shell 110, and then introduced into the interior of the inner protector 160 through the gas introduction holes 167 of the inner protector 160.

FIG. 3 is a view showing a route (gas route) along which the exhaust gas G within the exhaust pipe flows through the gas sensor 100 (the inner protector 160 and the outer protector 170) of the present embodiment. As shown in FIG. 3, the exhaust gas G having flowed through the exhaust pipe from the upstream side thereof (the left side in FIG. 3) toward the gas sensor 100 is introduced into the space S1 (the space between the first side wall portion 174 of the outer protector 170 and the side wall portion 161 of the inner protector 160) through the gas introduction holes 177 of the outer protector 170.

The exhaust gas G then flows within the space S1 toward the axially base end side (the upper side in FIG. 3), and is introduced into an internal space S3 of the inner protector 160 through the gas introduction holes 167 of the inner protector 160. Notably, a portion of the exhaust gas G is introduced into the gas introduction space S2 of the metallic shell 110, and is then introduced into the interior of the inner protector 160 through the gas introduction holes 167 of the inner protector 160. After that, the exhaust gas G flows within the internal space S3 toward the axially forward end side (the lower side in FIG. 3), and is discharged to the outside of the inner protector 160 through the discharge hole 166 of the inner protector 160. Subsequently, the exhaust gas G is introduced into a space S4 (the space between the taper wall 172 of the outer protector 170 and the bottom portion 162 of the inner protector 160), and is then discharged to the outside through the gas discharge hole 176 of the outer protector 170.

Notably, the diameter of the taper wall 172 of the outer protector 170 decreases toward the forward end side in the axial direction. Therefore, as indicated by arrows in FIG. 3, in a region outside the outer protector 170 (within the exhaust pipe), the flow velocity of the exhaust gas G increases in the vicinity of the forward end of the taper wall 172 (in the vicinity of the gas discharge hole 176), and due to the Venturi effect, a strong negative pressure can be produced in the vicinity of the forward end of the taper wall 172 (in the vicinity of the gas discharge hole 176). As a result, the exhaust gas G introduced into the internal space S3 is effectively and quickly discharged to the outside of the outer protector 170 while being drawn toward the gas discharge hole 176 located at the forward end of the taper wall 172.

As described above, the gas sensor 100 of the present embodiment is configured such that the exhaust gas G introduced from the outside into the gas introduction space S2 is introduced into the interior of the inner protector 160 through the gas introduction holes 167 of the inner protector 160, flows along the forward end portion 121 (a portion including the gas passage portions 123) of the detection element 120, and is then discharged to the outside of the inner protector 160 through the gas discharge hole 166 located on the forward end side with respect to the forward end 120b of the detection element 120 (FIG. 3).

In addition, as viewed in the axial direction of the detection element 120, the base end of the forward end portion 121 of the detection element 120 is located on the base end side with respect to the forward end 167b of each gas introduction hole 167 of the inner protector 160, and the forward end of the forward end portion 121 is located on the forward end side with respect to the base end 167c of each gas introduction hole 167 of the inner protector 160. In particular, as viewed in the axial direction of the detection element 120, the base end 123c of each gas passage portion 123 of the detection element 120 is located on the base end side with respect to the forward end 167b of each gas introduction hole 167 of the inner protector 160, and the forward end 123b of each gas passage portion 123 is located on the forward end side with respect to the base end 167c of each gas introduction hole 167 of the inner protector 160 (see FIGS. 2 and 3). By virtue of this positional relation, a portion of the exhaust gas G introduced into the interior of the inner protector 160 through the gas introduction holes 167 can be properly directed to flow along the forward end portion 121 (the gas passage portions 123).

Notably, in FIG. 2, the position of the forward end 167b of each gas introduction hole 167 in the axial direction is indicated by a straight line L2. FIG. 2 clearly shows that the base end 123c of the gas passage portion 123 is located on the base end side with respect to the straight line L2. Further, the position of the base end 167c of each gas introduction hole 167 in the axial direction is indicated by a straight line L3. FIG. 2 clearly shows that the forward end 123b of each gas passage portion 123 is located on the forward end side with respect to the straight line L3.

In addition, since the exhaust gas G passes through the gas introduction holes 167 of the inner protector 160 after having been introduced into the gas introduction space S2, the flow of the exhaust gas G assumes a straightened flow (laminar flow). Thus, the flow of the exhaust gas G assumes a straightened flow (laminar flow) around the forward end portion 121 (the gas passage portions 123) of the detection element 120. This is because, unlike the above-described gas sensor of Patent Document 2, after passing through the gas introduction holes 167 of the inner protector 160, the exhaust gas G flows toward the forward end portion 121 (the gas passage portions 123) of the detection element 120 without passing through the gas introduction space S2 of the metallic shell 110. As a result, the exhaust gas G can be caused to smoothly flow along the forward end portion 121

(the gas passage portions 123). Accordingly, the gas sensor 100 of the embodiment can have excellent responsiveness.

Further, in the gas sensor 100 of the present embodiment, the forward-end-side inner surface 113b of the forward end portion 113 of the metallic shell 110, which forms the gas introduction space S2, is a taper surface 113b whose diameter decreases from the forward end side toward the base end side thereof (see FIGS. 2 and 3). Therefore, the exhaust gas G introduced into the gas introduction space S2 is more likely to flow radially inward along the taper surface 113b. Thus, the exhaust gas G is more likely to be introduced into the interior of the inner protector 160 through the gas introduction holes 167 of the inner protector 160, which are located on the radially inner side of the taper surface 113b. This configuration further enhances the responsiveness of the gas sensor.

Furthermore, as shown in FIG. 2, in the gas sensor 100 of the present embodiment, the base end 167c of each gas introduction hole 167 of the inner protector 160 is located at the same position as the base end S2E of the gas introduction space S2 (corresponding to the base end 113c of the taper surface 113b of the metallic shell 110 which forms the gas introduction space S2) as viewed in the axial direction. Namely, the base end S2E of the gas introduction space S2 (the base end 113c of the taper surface 113b of the metallic shell 110) is located on the straight line L3. Therefore, the exhaust gas G introduced into the gas introduction space S2 is more likely to be smoothly introduced into the interior of the inner protector 160 through the gas introduction holes 167 of the inner protector 160 after flowing radially inward along the taper surface 113b. This enhances the responsiveness of the gas sensor.

Furthermore, in the gas sensor 100 of the present embodiment, as shown in FIG. 2, the forward end portion 161b of the side wall portion 161 of the inner protector 160 and the second side wall portion 175 of the outer protector 170 surrounding the circumference of the inner protector 160 are fixed together through press-fitting, and the outer protector 170 is welded to the metallic shell 110. This configuration can prevent the detection element 120 from being exposed directly to the gas-to-be-detected, and can prevent cracking which might otherwise occur if water contained in the gas-to-be-detected were to adhere to the detection element. In addition, the circumference of the inner protector 160 can be readily covered with the outer protector 170.

(First Modified Embodiment)

Next, a first modified embodiment of the present invention will be described. A gas sensor 200 of the present first modified embodiment is identical to the gas sensor 100 of the embodiment except for the inner protector. Therefore, only points which differ from the embodiment will mainly be described, and the description of the remaining portions will be omitted or simplified.

Figure 4:
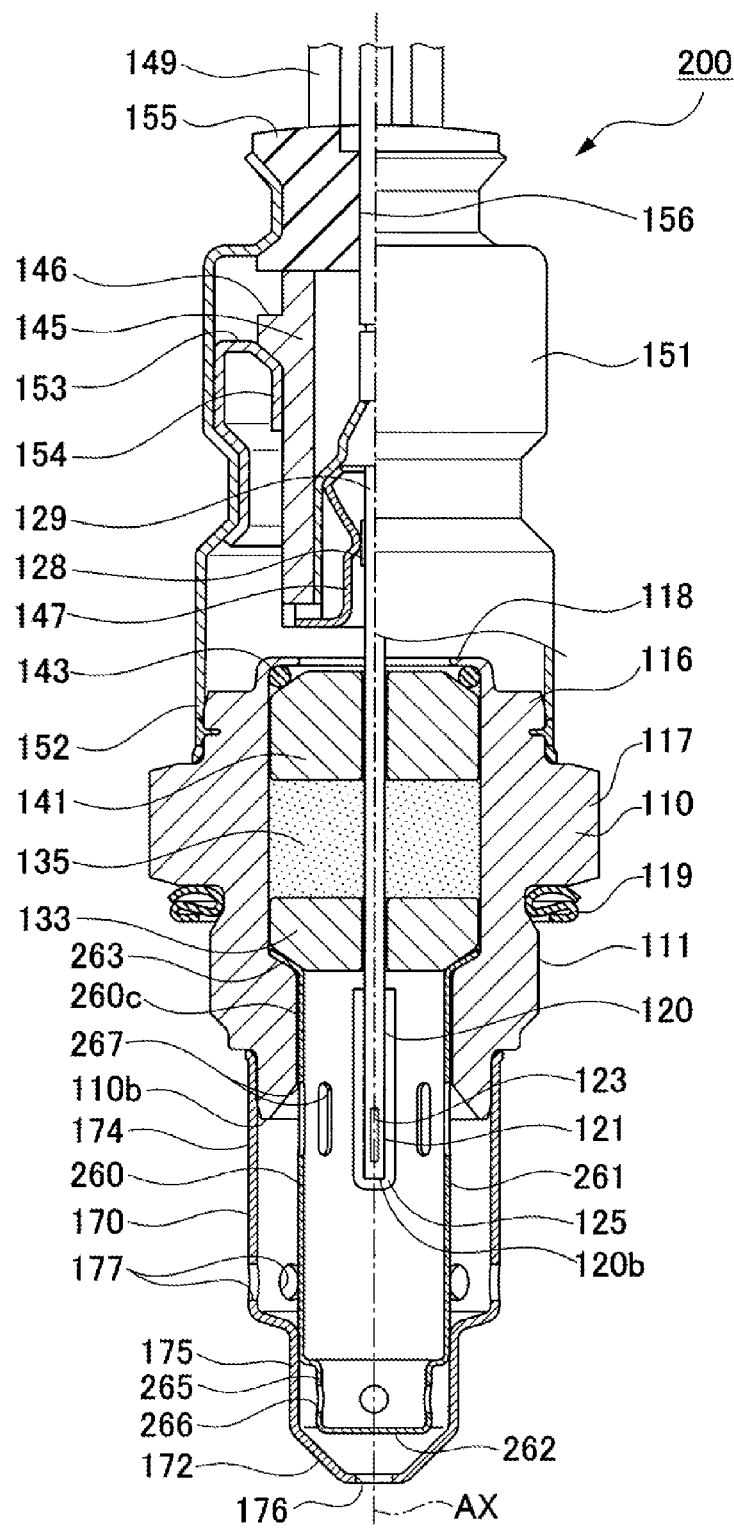
FIG. 4 is a partial sectional view of a gas sensor according to a first modified embodiment.
Figure 5:
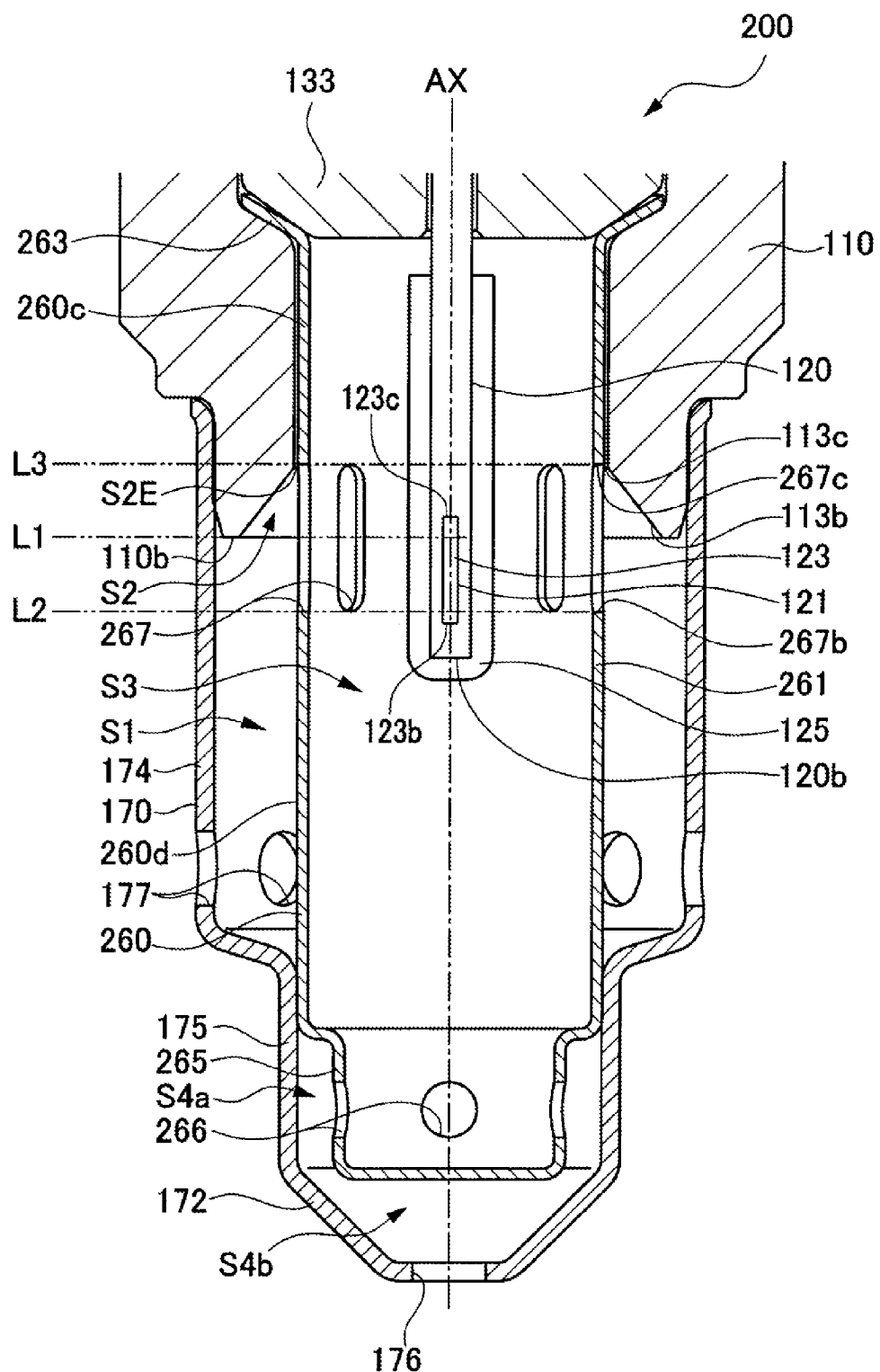
FIG. 5 is an enlarged sectional view of a forward end portion of the gas sensor of the first modified embodiment.

As shown in FIGS. 4 and 5, the inner protector 260 of the present first modified embodiment has a tapered annular flange portion 263 whose diameter increase toward the base end side (the upper side in FIGS. 4 and 5), a cylindrical tubular first side wall portion 261 which is located on the forward end side (the lower side in FIGS. 4 and 5) of the flange portion 263 and which extends in the axial direction (the direction along the axis AX), a second side wall portion 265 located on the axially forward end side of the first side wall portion 261, and a disk-shaped bottom portion 262 which closes the forward end side of the second side wall portion 265. The inner protector 260 is fixed to the metallic shell 110 in a state in which its flange portion 263 is sandwiched between the ceramic ring 133 and the metallic shell 110, and the forward end portion 121 of the detection element 120 is disposed in the internal space S3 of the inner protector 260 (see FIGS. 4 and 5).

Gas introduction holes 267 for introducing the exhaust gas G (the gas-to-be-detected) from the outside of the inner protector 260 into the interior thereof are formed in the first side wall portion 261 at positions on the base end side with respect to the forward end 120b of the detection element 120. Notably, in the present first modified embodiment, eight gas introduction holes 267 having the same dimension are formed at equal intervals in the circumferential direction of the first side wall portion 261 at the same position in the axial direction. At least a portion of each of these gas introduction holes 267 is located on the base end side with respect to the forward end 110b of the metallic shell 110.

Further, the inner protector 260 has gas discharge holes 266 for discharging the exhaust gas G from the interior of the inner protector 260 to the outside thereof. The gas discharge holes 266 are located on the forward end side with respect to the forward end 120b of the detection element 120. More specifically, the gas discharge holes 266 are provided in the second side wall portion 265 of the inner protector 260. Notably, in the present first modified embodiment, six gas discharge holes 266 having the same dimension are formed at equal intervals in the circumferential direction of the second side wall portion 265 at the same position in the axial direction.

In the present first modified embodiment as well, at least a portion of the forward end portion 121 (each gas passage portion 123) of the detection element 120 is located on the base end side (on the upper side in FIGS. 4 and 5) in relation to the forward end 110b of the metallic shell 110. Notably, in FIG. 5, the position of the forward end 110b of the metallic shell 110 in the axial direction is indicated by a straight line L1. FIG. 5 clearly shows that a portion of the gas passage portion 123 is located on the base end side with respect to the straight line L1.

Notably, in the present first modified embodiment, the inner protector 260 corresponds to the "protector" of the invention.

In the case of the gas sensor 200 of the present first modified embodiment as well, the base end portion 260c of the inner protector 260 is disposed in (inserted into) the space inside the metallic shell 110 as shown in FIG. 5. This configuration enables at least a portion of each gas introduction hole 267 of the inner protector 260 to be disposed on the base end side with respect to the forward end 110b of the metallic shell 110 (namely, in the interior of the metallic shell 110).

In addition, the forward-end-side inner surface 113b of a forward end portion 113 of the metallic shell 110 is concaved radially outward, and forms a gas introduction space S2 in cooperation with the outer surface 260d of the inner protector 260 (between the forward-end-side inner surface 113b and the outer surface 260d). This gas introduction space S2 is a space for introducing the exhaust gas G (the gas-to-be-detected) from a region on the forward end side of the metallic shell 110 into the gas introduction holes 267 of the inner protector 260. Namely, at least a portion of each gas introduction hole 267 of the inner protector 260 is exposed to the gas introduction space S2. By virtue of such a structure, in the gas sensor 200 of the present first modified embodiment as well, as indicated by arrows in FIG. 6, the exhaust gas G (at least a portion thereof) can be introduced into the gas introduction space S2 of the metallic shell 110, and then introduced into the interior of the inner protector 260 through the gas introduction holes 267 of the inner protector 260.

Figure 6:
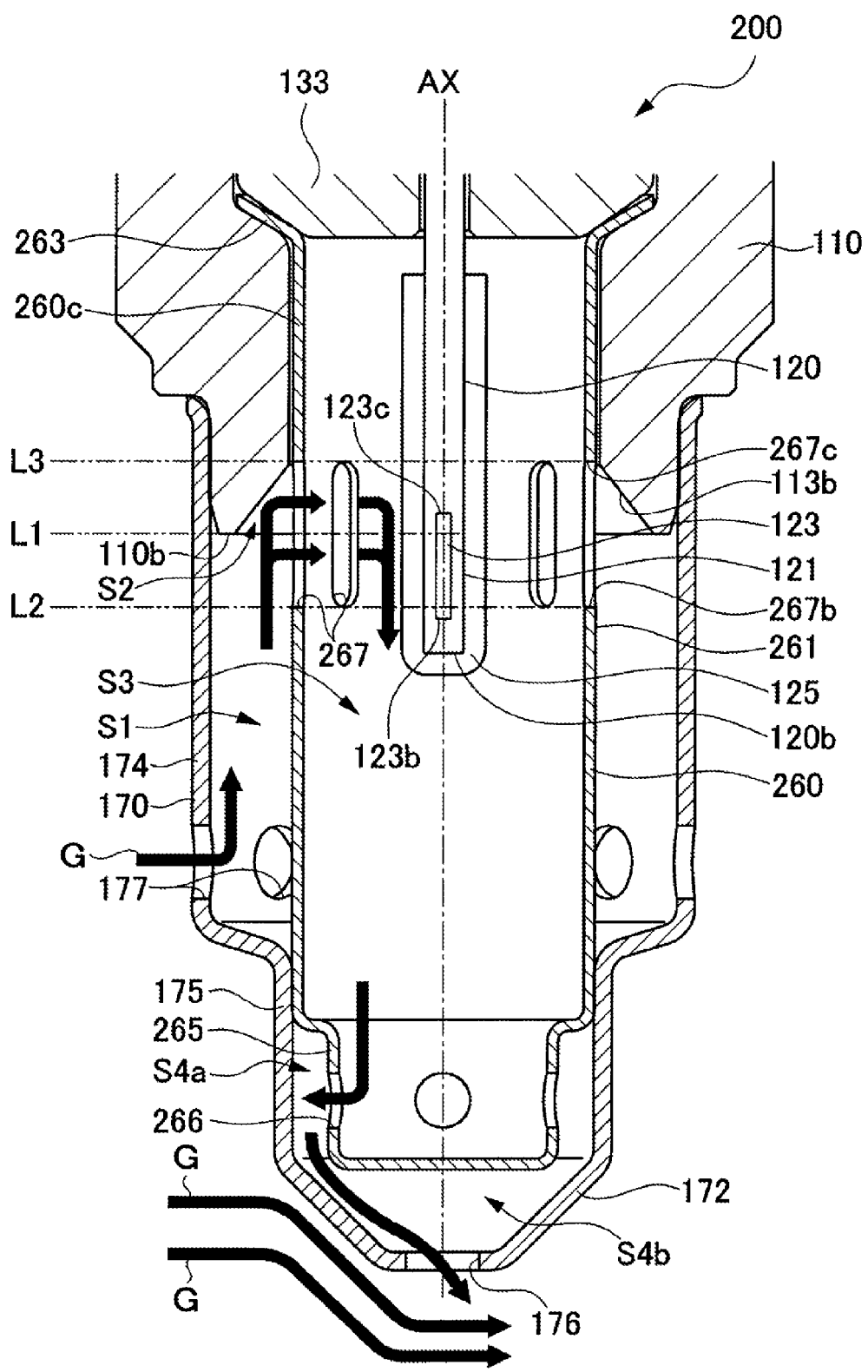
FIG. 6 is a view describing a flow of a gas-to-be-detected within the gas sensor of the first modified embodiment.

Notably, FIG. 6 is a view showing a route (gas route) along which the exhaust gas G within the exhaust pipe flows through the gas sensor 200 (the inner protector 260 and the outer protector 170). As shown in FIG. 6, the exhaust gas G having flowed through the exhaust pipe from the upstream side thereof (the left side in FIG. 6) toward the gas sensor 200 is introduced into the space S1 (the space between the first side wall portion 174 of the outer protector 170 and the first side wall portion 261 of the inner protector 260) through the gas introduction holes 177 of the outer protector 170.

The exhaust gas G then flows within the space S1 toward the axially base end side (the upper side in FIG. 6), and is introduced into the internal space S3 of the inner protector 260 through the gas introduction holes 267 of the inner protector 260. Notably, a portion of the exhaust gas G is introduced into the gas introduction space S2 of the metallic shell 110, and is then introduced into the interior of the inner protector 260 through the gas introduction holes 267 of the inner protector 260.

Further, the exhaust gas G flows within the internal space S3 toward the axially forward end side (the lower side in FIG. 6), and is discharged to the outside of the inner protector 260 through the discharge holes 266 of the inner protector 260. Subsequently, the exhaust gas G is introduced into a space S4*a* (the space between the second side wall portion 175 of the outer protector 170 and the second side wall portion 265 of the inner protector 260, flows through a space S4*b* (the space between the taper wall 172 of the outer protector 170 and the bottom portion 262 of the inner protector 260), and is then discharged to the outside through the gas discharge hole 176 of the outer protector 170.

As described above, the gas sensor 200 of the present first modified embodiment is also configured such that the exhaust gas G introduced from the outside into the gas introduction space S2 is introduced into the interior of the inner protector 260 through the gas introduction holes 267 of the inner protector 260, flows along the forward end portion 121 (a portion including the gas passage portions 123) of the detection element 120, and is then discharged to the outside of the inner protector 260 through the gas discharge holes 266 located on the forward end side with respect to the forward end 120*b* of the detection element 120 (FIG. 6).

In addition, as viewed in the axial direction of the detection element 120, the base end of the forward end portion 121 of the detection element 120 is located on the base end side with respect to the forward end 267*b* of each gas introduction hole 267 of the inner protector 260, and the forward end of the forward end portion 121 is located on the forward end side with respect to the base end 267*c* of each gas introduction hole 267 of the inner protector 260. In particular, as viewed in the axial direction of the detection element 120, the base end 123*c* of each gas passage portion 123 of the detection element 120 is located on the base end side with respect to the forward end 267*b* of each gas introduction hole 267 of the inner protector 260, and the forward end 123*b* of each gas passage portion 123 is located on the forward end side with respect to the base end 267*c* of each gas introduction hole 267 of the inner protector 260 (see FIGS. 5 and 6). By virtue of this positional relation, a portion of the exhaust gas G introduced into the interior of the inner protector 260 through the gas introduction holes 267 can be properly directed to flow along the forward end portion 121 (the gas passage portions 123).

Notably, in FIG. 5, the position of the forward end 267*b* of each gas introduction hole 267 in the axial direction is indicated by a straight line L2. FIG. 5 clearly shows that the base end 123*c* of the gas passage portion 123 is located on the base end side with respect to the straight line L2. Further, the position of the base end 267*c* of each gas introduction hole 267 in the axial direction is indicated by a straight line L3. FIG. 5 clearly shows that the forward end 123*b* of each gas passage portion 123 is located on the forward end side with respect to the straight line L3.

In addition, since the exhaust gas G passes through the gas introduction holes 267 of the inner protector 260 after having been introduced into the gas introduction space S2, the flow of the exhaust gas G assumes a straightened flow (laminar flow). Thus, the flow of the exhaust gas G assumes a straightened flow (laminar flow) around the gas passage portions 123 of the detection element 120. As a result, the exhaust gas G can be directed to smoothly flow along the forward end portion 121 (the gas passage portions 123). Accordingly, the gas sensor 200 of the present first modified embodiment also can have excellent responsiveness.

Further, in the gas sensor 200 of the present first modified embodiment as well, the forward-end-side inner surface 113*b* of the forward end portion 113 of the metallic shell 110, which forms the gas introduction space S2, is a taper surface 113*b* whose diameter decreases from the forward end side toward the base end side thereof (see FIGS. 5 and 6). Therefore, the exhaust gas G introduced into the gas introduction space S2 is more likely to flow radially inward along the taper surface 113*b*. Thus, the exhaust gas G is more likely to be introduced into the interior of the inner protector 260 through the gas introduction holes 267 of the inner protector 260, which are located on the radially inner side of the taper surface 113*b*. This configuration further enhances the responsiveness of the gas sensor.

Furthermore, as shown in FIG. 5, in the gas sensor 200 of the present first modified embodiment, the base end 267*c* of each gas introduction hole 267 of the inner protector 260 is located at the same position as the base end S2E of the gas introduction space S2 (corresponding to the base end 113*c* of the taper surface 113*b* of the metallic shell 110 which forms the gas introduction space S2) as viewed in the axial direction. Namely, the base end S2E of the gas introduction space S2 (the base end 113*c* of the taper surface 113*b* of the metallic shell 110) is located on the straight line L3. Therefore, the exhaust gas G introduced into the gas introduction space S2 is more likely to be smoothly introduced into the interior of the inner protector 260 through the gas introduction holes 267 of the inner protector 260 after flowing radially inward along the taper surface 113*b*. This enhances the responsiveness of the gas sensor.

(Second Modified Embodiment)

Next, a second modified embodiment of the present invention will be described. A gas sensor 300 of the present second modified embodiment is identical with the gas sensor 100 of the embodiment except for the metallic shell and the protector. Therefore, only those points which differ from the embodiment will be mainly described, and the description of the remaining portions will be omitted or simplified.

In the gas sensor 100 of the embodiment, two protectors; i.e., the inner protector 160 and the outer protector 170, are provided (see FIG. 1). In contrast, the gas sensor 300 of the present second modified embodiment has a single protector 360 as shown in FIG. 7.

Also, a metallic shell 310 of the present second modified embodiment is longer than the metallic shell 110 of the embodiment in terms of the axial length (length in the vertical direction in FIG. 7) of a portion located on the base end side of the tool engagement portion 317. Further, the metallic shell 310 of the present second modified embodiment has a lager gas introduction space S2 as compared with the metallic shell 110 of the embodiment.

Figure 7:
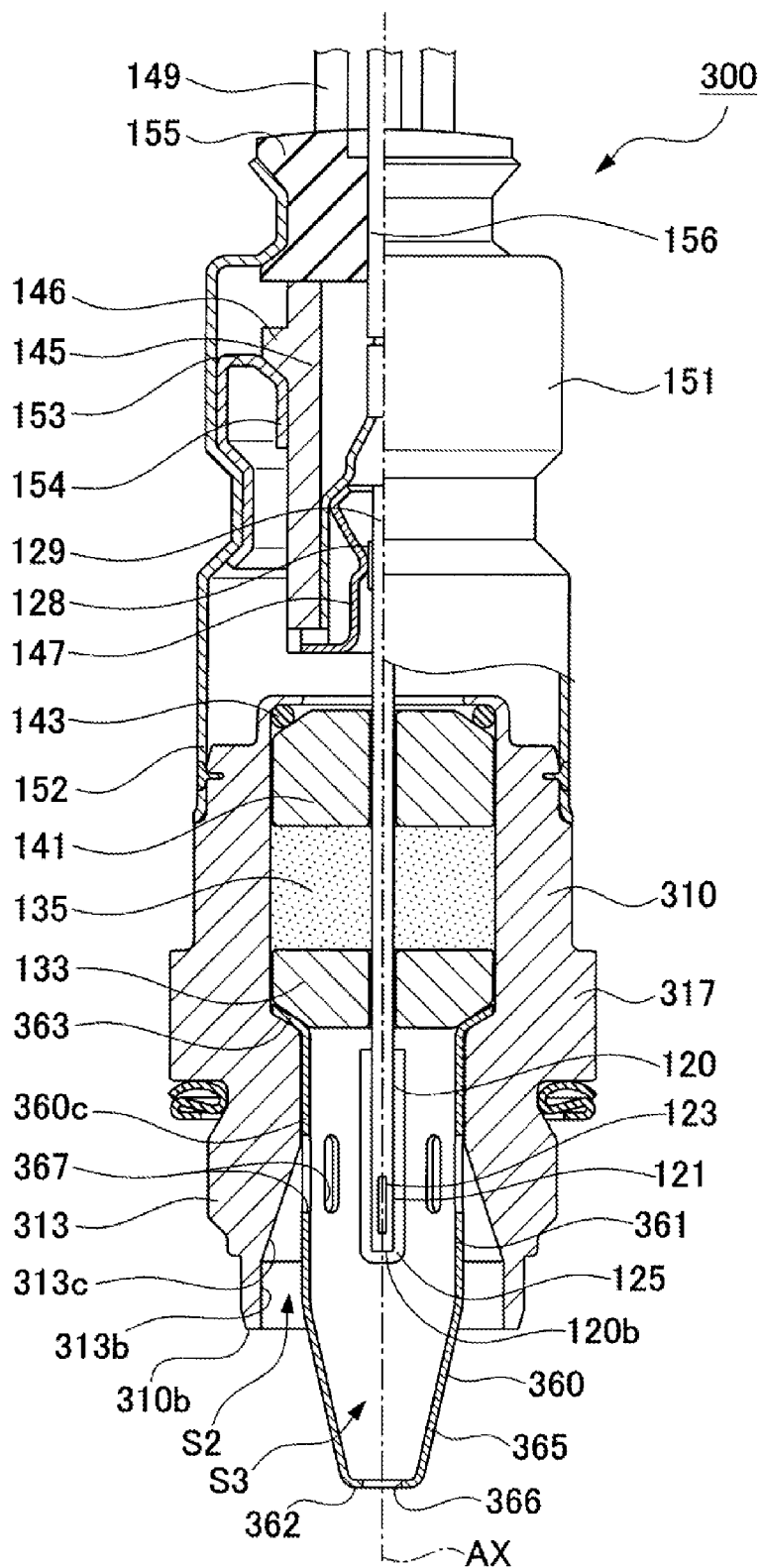
FIG. 7 is a partial sectional view of a gas sensor according to a second modified embodiment.
Figure 8:
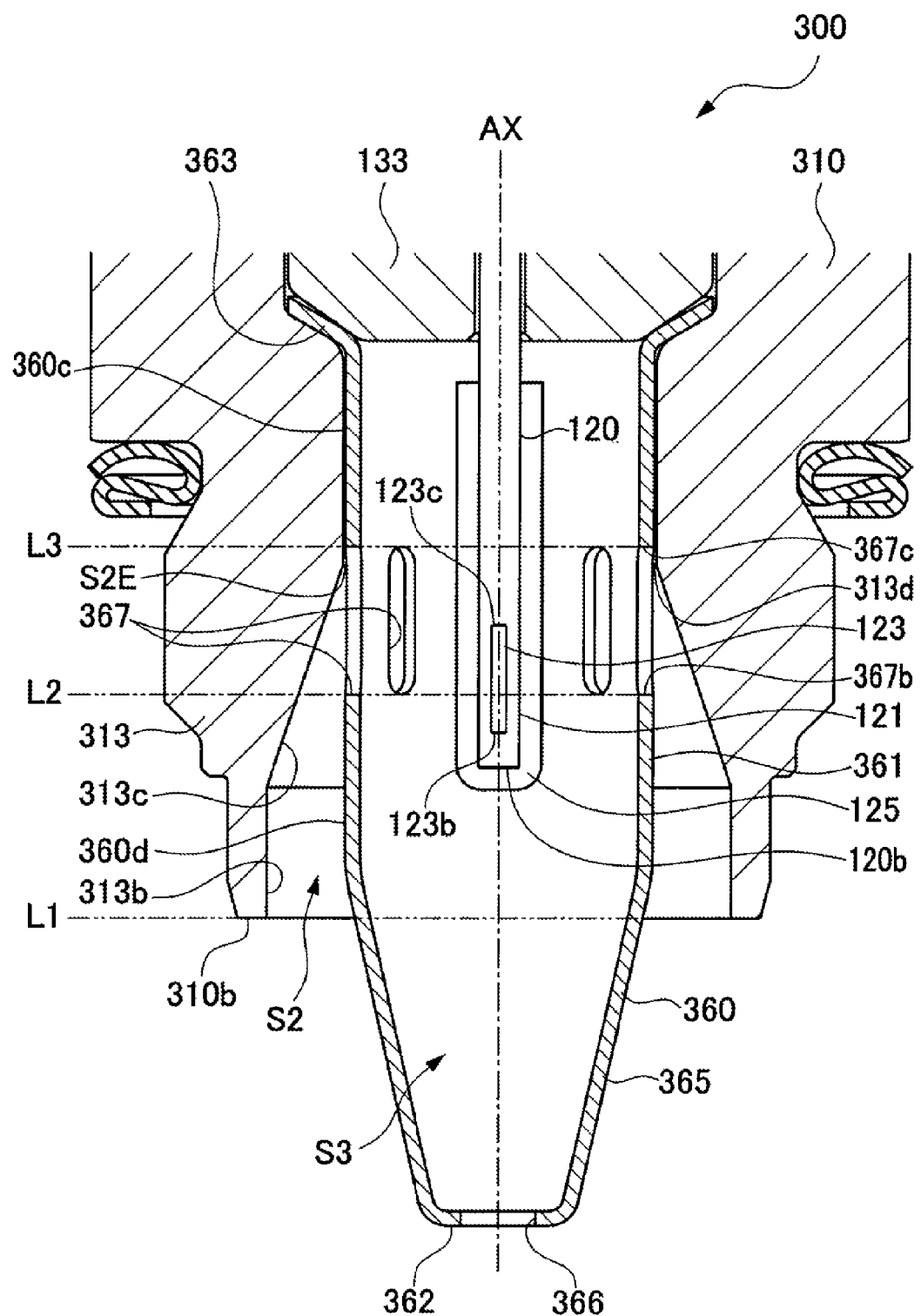
FIG. 8 is an enlarged sectional view of a forward end portion of the gas sensor of the second modified embodiment.

As shown in FIGS. 7 and 8, the protector 360 of the present second modified embodiment has a tapered annular flange portion 363 whose diameter increases toward the base end side (the upper side in FIGS. 7 and 8), a cylindrical tubular side wall portion 361 which is located on the forward end side (the lower side in FIGS. 7 and 8) of the flange portion 363 and extends in the axial direction (the direction along the axis AX), a taper wall 365 located on the axially forward end side of the side wall portion 361, and a bottom portion 362 located on the forward end side of the taper wall 365. The taper wall 365 has a tapered tubular shape (truncated conical tubular shape) such that its diameter decreases toward the axially forward end side.

The protector 360 is fixed to the metallic shell 310 in a state in which its flange portion 363 is sandwiched between the ceramic ring 133 and the metallic shell 310, and the forward end portion 121 of the detection element 120 is disposed in the internal space S3 of the protector 360 (see FIGS. 7 and 8).

Gas introduction holes 367 for introducing the exhaust gas G (the gas-to-be-detected) from the outside of the protector 360 into the interior thereof are formed in the side wall portion 361 of the protector 360 at positions on the base end side with respect to the forward end 120b of the detection element 120. Notably, in the present second modified embodiment as well, eight gas introduction holes 367 having the same dimension are formed at equal intervals in the circumferential direction of the side wall portion 361 at the same position in the axial direction. At least a portion (the entirety in the present second modified embodiment) of each of these gas introduction holes 367 is located on the base end side with respect to the forward end 310b of the metallic shell 310.

Further, the protector 360 has a gas discharge hole 366 for discharging the exhaust gas G from the interior of the protector 360 to the outside thereof. The gas discharge hole 366 is located on the forward end side with respect to the forward end 120b of the detection element 120. More specifically, the gas discharge hole 366 is provided in the bottom portion 362 of the protector 360.

In the present second modified embodiment as well, at least a portion (the entirety in the present second modified embodiment) of the forward end portion 121 (each gas passage portion 123) of the detection element 120 is located on the base end side (on the upper side in FIGS. 7 and 8) in relation to the forward end 310b of the metallic shell 310. Notably, in FIG. 8, the position of the forward end 310b of the metallic shell 310 in the axial direction is indicated by a straight line L1. FIG. 8 clearly shows that the entirety of each gas passage portion 123 is located on the base end side with respect to the straight line L1.

In the case of the gas sensor 300 of the present second modified embodiment as well, the base end portion 360c of the protector 360 is disposed in (inserted into) the space inside the metallic shell 310 as shown in FIG. 8. This configuration enables at least a portion of each gas introduction hole 367 of the protector 360 to be disposed on the base end side with respect to the forward end 310b of the metallic shell 310 (namely, in the interior of the metallic shell 310).

In addition, the forward-end-side inner surface 313b of the forward end portion 313 of the metallic shell 310 is concaved radially outward, and forms a gas introduction space S2 in cooperation with the outer surface 360d of the protector 360 (between the forward-end-side inner surface 313b and the outer surface 360d). This gas introduction space S2 is a space for introducing the exhaust gas G (the gas-to-be-detected) from a region on the forward end side of the metallic shell 310 into the gas introduction holes 367 of the protector 360. Namely, at least a portion (the entirety in the present second modified embodiment) of each gas introduction hole 367 of the protector 360 is exposed to the gas introduction space S2. By virtue of such a structure, in the gas sensor 300 of the present second modified embodiment as well, as indicated by arrows in FIG. 9, the exhaust gas G can be introduced into the gas introduction space S2 of the metallic shell 310, and then introduced into the interior of the protector 360 through the gas introduction holes 367 of the protector 360.

Figure 9:
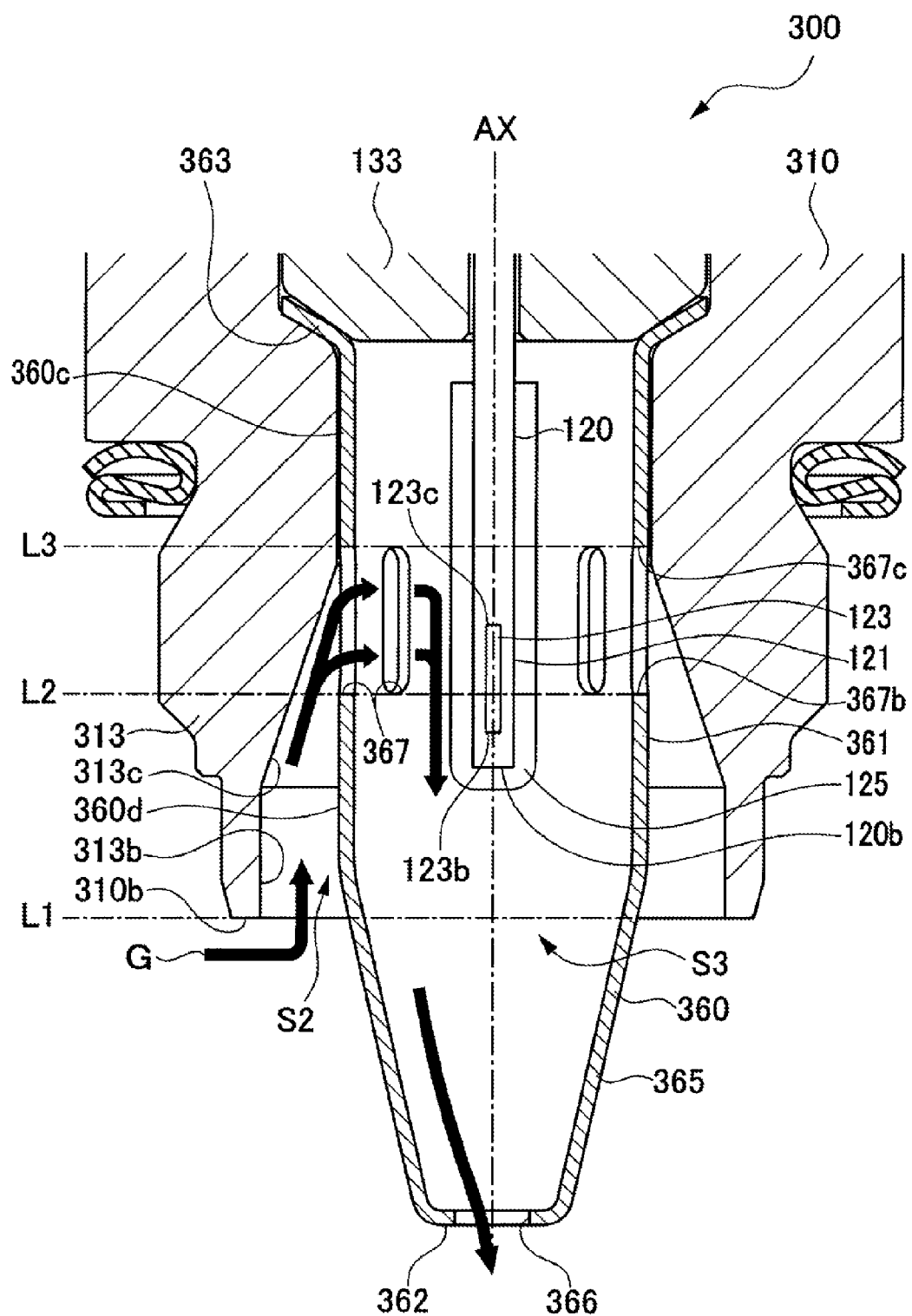
FIG. 9 is a view describing a flow of a gas-to-be-detected within the gas sensor of the second modified embodiment.

Notably, FIG. 9 is a view showing a route (gas route) along which the exhaust gas G within the exhaust pipe flows through the gas sensor 300 (the metallic shell 310 and the protector 360). As shown in FIG. 9, the exhaust gas G having flowed through the exhaust pipe from the upstream side thereof (the left side in FIG. 9) toward the gas sensor 300 is introduced into the gas introduction space S2 of the metallic shell 310, then flows within the gas introduction space S2 toward the axially base end side (the upper side in FIG. 9), and is introduced into an internal space S3 of the protector 360 through the gas introduction holes 367 of the protector 360. After that, the exhaust gas G flows within the internal space S3 toward the axially forward end side (the lower side in FIG. 9), and is discharged to the outside of the protector 360 through the discharge hole 366 of the protector 360.

As described above, the gas sensor 300 of the present second modified embodiment is also configured such that the exhaust gas G introduced from the outside into the gas introduction space S2 is introduced into the interior of the protector 360 through the gas introduction holes 367 of the protector 360, flows along the forward end portion 121 (a portion including the gas passage portions 123) of the detection element 120, and is then discharged to the outside of the protector 360 through the gas discharge hole 366 located on the forward end side with respect to the forward end 120b of the detection element 120 (FIG. 9).

In addition, as viewed in the axial direction of the detection element 120, the base end of the forward end portion 121 of the detection element 120 is located on the base end side with respect to the forward end 367b of each gas introduction hole 367 of the protector 360, and the forward end of the forward end portion 121 is located on the forward end side with respect to the base end 367c of each gas introduction hole 367 of the protector 360. In particular, as viewed in the axial direction of the detection element 120, the base end 123c of each gas passage portion 123 of the detection element 120 is located on the base end side with respect to the forward end 367b of each gas introduction hole 367 of the protector 360, and the forward end 123b of each gas passage portion 123 is located on the forward end side with respect to the base end 367c of each gas introduction hole 367 of the protector 360 (see FIGS. 8 and 9). By virtue of this positional relation, a portion of the exhaust gas G introduced into the interior of the protector 360 through the gas introduction holes 367 can be properly directed to flow along the forward end portion 121 (the gas passage portions 123).

Notably, in FIG. 8, the position of the forward end 367b of each gas introduction hole 367 in the axial direction is indicated by a straight line L2. FIG. 8 clearly shows that the base end 123c of the gas passage portion 123 is located on the base end side with respect to the straight line L2. Further, the position of the base end 367c of each gas introduction hole 367 in the axial direction is indicated by a straight line L3. FIG. 8 clearly shows that the forward end 123b of each gas passage portion 123 is located on the forward end side with respect to the straight line L3.

In addition, since the exhaust gas G passes through the gas introduction holes 367 of the protector 360 after having been introduced into the gas introduction space S2, the flow of the exhaust gas G assumes a straightened flow (laminar flow). Thus, the flow of the exhaust gas G assumes a straightened flow (laminar flow) around the gas passage portions 123 of the detection element 120. As a result, the exhaust gas G can be directed to smoothly flow along the forward end portion 121 (the gas passage portions 123). Accordingly, the gas sensor 300 of the present second modified embodiment also can have excellent responsiveness.

Further, in the gas sensor 300 of the present second modified embodiment, the forward-end-side inner surface 313b of the forward end portion 313 of the metallic shell 310, which forms the gas introduction space S2, has a taper surface 313c whose diameter decreases from the forward end side toward the base end side thereof (see FIGS. 8 and 9). Therefore, the exhaust gas G introduced into the gas introduction space S2 is more likely to flow radially inward along the taper surface 313c. Thus, the exhaust gas G is more likely to be introduced into the interior of the protector 360 through the gas introduction holes 367 of the protector 360, which are located on the radially inner side of the taper surface 313c. This configuration further enhances the responsiveness of the gas sensor.

Furthermore, as shown in FIG. 8, in the gas sensor 300 of the present second modified embodiment, the base end 367c of each gas introduction hole 367 of the protector 360 is located on the base end side (the upper side in FIG. 8) of the base end S2E of the gas introduction space S2 (corresponding to the base end 313d of the forward-end-side inner surface 313b of the metallic shell 310 which forms the gas introduction space S2) as viewed in the axial direction. Therefore, the exhaust gas G introduced into the gas introduction space S2 is more likely to be smoothly introduced into the interior of the protector 360 through the gas introduction holes 367 of the protector 360 after flowing radially inward along the taper surface 313c. This enhances the responsiveness of the gas sensor.

Although the present invention has been described in detail with reference to the above embodiment and first and second modified embodiments, the present invention should not be construed as being limited thereto. It should be apparent to those skilled in the art that various changes in form and detail of the invention as shown and described above may be made. It is intended that such changes be included within the spirit and scope of the claims appended hereto.

For example, in the embodiment, etc., the gas sensor is a full-range air/fuel ratio sensor. However, the present invention can be applied to oxygen sensors, NOx sensors, HC sensors, etc.

In the embodiment and the modified embodiments, the inner protector is inserted into (disposed in) the interior of the metallic shell. However, the present invention can be applied to a structure in which the inner protector is press-fitted into the interior of the metallic shell.

In the embodiment and the modified embodiments, the gas passage portion 123 is a "porous body provided in a passage for establishing communication between the outside of the detection element and a gas measurement chamber provided in the detection element 120." However, the present invention can be applied to the case where the gas passage portion is a "porous portion which is provided to be exposed on the surface of a detection element and which intervenes between the electrode provided inside the detection element and the outside of the detection element." Examples of such a porous portion include an electrode protection layer described in FIG. 1 of U.S. Publication No. US 2007/0017806 corresponding to Japanese Patent Application Laid-Open (kokai) No. 2007-33114 and a diffusion resistor layer described in FIG. 3 of U.S. Publication No. US. 2004/0123642 corresponding to Japanese Patent Application Laid-Open (kokai) No. 2004-191328, the above-noted applications incorporated herein by reference. Also, the present invention can be applied to the case where the gas passage portion is a "passage which connects a gas measurement chamber provided in a detection element and the outside of the detection element." Examples of such a passage includes an outside communication portion described in FIG. 3 of U.S. Publication No. US 2011/0233060 corresponding to Japanese Patent Application Laid-Open (kokai) No. 2011-227061 and a gas flow hole described in FIG. 1 of U.S. Publication No. US 2008/0296156 corresponding to Japanese Patent Application Laid-Open (kokai) No. 2008-298781, the above-noted applications incorporated herein by reference.

In the embodiment and the modified embodiments, a plate-type detection element having gas passage portions 123 at a forward end portion 121 thereof is used. However, the present invention can be applied to a plate-type detection element which has no gas passage portion at a forward end portion thereof and a known tube-type detection element.

This application is based on Japanese Patent Application No. 2013-084599 filed Apr. 15, 2013, incorporated herein by reference in its entirety.

What is claimed is:
1. A gas sensor comprising:
    a detection element which extends from a base end side to a forward end side in an axial direction, which detects a particular gas component contained in a gas-to-be-detected, and which has a detection section on the forward end side thereof;
    a tubular metallic shell which surrounds a circumference of the detection element; and
    a tubular protector which surrounds a circumference of a forward end portion of the detection element,
    the protector having a gas introduction hole located on the base end side with respect to a forward end of the detection element and which introduces the gas-to-be-detected from outside of the protector into the interior thereof, and a gas discharge hole located on the forward end side with respect to the forward end of the detection element and which discharges the gas-to-be- detected from the interior of the protector to the outside thereof, wherein
    at least a portion of the detection section of the detection element is located in an interior of a forward end of the metallic shell;
    the protector is inserted into the interior of the metallic shell in a state in which at least a portion of the gas introduction hole is located on the base end side with respect to the forward end of the metallic shell;
    a forward-end-side inner surface of the metallic shell and an outer surface of the protector form there between a gas introduction space for guiding the gas-to-be-de- tected from a region on the forward end side with respect to the metallic shell to the gas introduction hole of the protector; and a base end of the detection section of the detection element is located on the base end side with respect to a forward end of the gas introduction hole, and a forward end of the detection section is located on the forward end side with respect to a base end of the gas introduction hole.

2. The gas sensor as claimed in claim 1, wherein the detection section has a gas passage portion which allows passage of the gas-to-be-detected therethrough;

at least a portion of the gas passage portion is located on the base end side with respect to the forward end of the metallic shell; and a base end of the gas passage portion is located on the base end side with respect to the forward end of the gas introduction hole, and a forward end of the gas passage portion is located on the forward end side with respect to the base end of the gas introduction hole.

3. The gas sensor as claimed in claim 1, wherein the forward-end-side inner surface of the metallic shell which forms the gas introduction space has a taper surface whose diameter decreases from the forward end side toward the base end side.

4. The gas sensor as claimed in claim 1, wherein the base end of the gas introduction hole of the protector is located at a position which is the same as, or is shifted toward the base end side from, the position of a base end of the gas introduction space in the axial direction.

5. The gas sensor as claimed in claim 1, further comprising an outer protector which covers a circumference of the protector and which is welded to the metallic shell, wherein the protector is fixedly press-fitted into the outer protector.

6. The gas sensor as claimed in claim 1, wherein, as viewed in the axial direction, the forward end of the detection element projects from the forward end of the metallic shell by a projection length of 5 mm or less.

* * * * *